(12) United States Patent
Mo

(10) Patent No.: US 6,862,477 B1
(45) Date of Patent: *Mar. 1, 2005

(54) MULTI-SITE CARDIAC STIMULATION DEVICE AND METHOD FOR DETECTING RETROGRADE CONDUCTION

(75) Inventor: Anthony Mo, Fremont, CA (US)

(73) Assignee: Pacesetter, Inc., Sylmar, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 10/310,429

(22) Filed: Dec. 4, 2002

Related U.S. Application Data

(63) Continuation of application No. 09/881,449, filed on Jun. 13, 2001, now Pat. No. 6,611,714.

(51) Int. Cl.[7] ............................................. A61N 1/365
(52) U.S. Cl. ....................................................... 607/27
(58) Field of Search ............................... 607/9, 14, 17, 607/18, 25, 27; 600/515

(56) References Cited

U.S. PATENT DOCUMENTS

| | | | |
|---|---|---|---|
| 4,453,963 A | 6/1984 | Larson et al. ................... | 65/29 |
| 4,788,980 A | 12/1988 | Mann et al. .......... | 128/419 PG |
| 4,940,052 A | 7/1990 | Mann et al. .......... | 128/419 PG |
| 5,074,308 A | 12/1991 | Sholder et al. ............. | 128/697 |
| 5,129,393 A | 7/1992 | Brumwell ............. | 128/419 PG |
| 5,228,438 A * | 7/1993 | Buchanan ..................... | 607/18 |
| 5,312,450 A | 5/1994 | Markowitz ................... | 607/14 |
| 5,466,254 A | 11/1995 | Helland ...................... | 607/123 |
| 5,476,482 A | 12/1995 | Lu ................................ | 607/9 |
| 5,496,350 A | 3/1996 | Lu .............................. | 607/14 |
| 5,507,783 A | 4/1996 | Buchanan ..................... | 607/14 |
| 5,514,164 A | 5/1996 | Mann et al. .................. | 607/25 |
| 5,573,550 A | 11/1996 | Zadeh et al. .................. | 607/28 |
| 5,653,738 A | 8/1997 | Sholder ........................ | 607/14 |
| 5,685,315 A | 11/1997 | McClure et al. ............ | 128/708 |
| 6,115,632 A * | 9/2000 | Akers et al. ..................... | 607/9 |

OTHER PUBLICATIONS

Ramdat Misier, A. MD, PhD, et al., Multisite or Alternate Site Pacing for the Prevention of Atrial Fibrillation, American Journal of Cardiology, vol. 83 (5B), pp:237D–240D (Mar. 11, 1999).

* cited by examiner

Primary Examiner—George Manuel

(57) ABSTRACT

An implantable cardiac stimulation device, such as a pacemaker, defibrillator and/or cardioverter, and an associated method that provide cardiac stimulation to at least two ventricular stimulation sites, within a single ventricle or across two ventricles. A high intrinsic atrial rate triggers a retrograde conduction detection routine when a high ventricular stimulation rate is sustained for a predetermined number of cycles during an atrial sensing mode. This routine interrupts concurrent stimulation, and alternates the stimulation output to the different ventricular sites.

20 Claims, 5 Drawing Sheets

MULTI-SITE CARDIAC STIMULATION DEVICE AND METHOD FOR DETECTING RETROGRADE CONDUCTION

CROSS-REFERENCE TO RELATED APPLICATIONS

This application is a continuation of U.S. patent application Ser. No. 09/881,449, filed Jun. 13, 2001, now U.S. Pat. No. 6,611,714.

FIELD OF THE INVENTION

The present invention relates generally to programmable cardiac stimulating devices. More specifically, this is directed to a multi-chamber or biventricular cardiac stimulation device and associated method for detecting retrograde conduction from one or more ventricular stimulation site for the purpose of identifying and terminating pacemaker-mediated tachycardia (PMT).

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. One or more heart chambers may be electrically stimulated depending on the location and severity of the conduction disorder.

A single-chamber pacemaker delivers pacing pulses to one chamber of the heart, either one atrium or one ventricle. Dual chamber pacemakers are now commonly available and can provide stimulation in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (a P-wave) is not detected by the atrial channel, a stimulating pulse will be delivered to depolarize the atrium and cause contraction. Following either a detected P-wave or an atrial pacing pulse, the ventricular channel attempts to detect a depolarization signal in the ventricle, known as an R-wave. If no R-wave is detected within a defined atrial-ventricular interval (AV interval, also referred to as AV delay), a stimulation pulse is delivered to the ventricle to cause ventricular contraction. In this way, atrioventricular synchrony is achieved by coordinating the delivery of ventricular output in response to a sensed or paced atrial event.

Unfortunately, a pacemaker operating in the DDD mode may contribute, in combination with other factors, to a pacemaker-mediated tachycardia (PMT). For example, in patients who are prone to atrial arrhythmias, e.g., a fast atrial rate, the DDD pacer tracks the fast atrial rate, causing the ventricles to be paced at a correspondingly fast rate, thereby causing a tachycardia (fast heart rate) to occur. Without the DDD pacemaker, such tachycardia would probably not occur because the ventricles would normally continue at a slower (more normal) rate, despite the fast atrial rate. However, with the DDD pacemaker, the stimulation of the ventricles occurs so as to track the fast atrial rate, and thus the pacemaker effectively intervenes or "mediates" so as to cause the tachycardia, appropriately termed a "pacemaker-mediated tachycardia," or PMT, to occur.

There are other reasons why a pacemaker-mediated tachycardia may be triggered by a DDD pacer, other than simply tracking a fast atrial rate. For example, prolonged intervals between atrial and ventricular depolarization can cause or enhance retrograde conduction of the depolarization wave back into the atria producing what is referred to as a "retrograde P-wave." A retrograde P-wave may be sensed by the atrial channel sensing circuits. Unfortunately, the pacemaker sensing circuits cannot differentiate between retrograde P-waves and normal P-waves, so such sensing may result in a pacemaker-mediated tachycardia wherein each ventricular paced event is followed by a retrograde P-wave which is tracked, resulting in another ventricular paced event, causing the process to repeat.

It is well known that the type of pacemaker-mediated tachycardia described above (resulting from sensing retrograde P-waves) can be prevented by programming the post ventricular atrial refractory period (PVARP) of the pacemaker to be longer than the retrograde conduction time. Such lengthening of the PVARP, however, disadvantageously prevents the sensing of a P-wave that occurs late in the PVARP. A failure to sense a P-wave, in turn, causes an atrial stimulus to be generated by the pacemaker that is more than likely delivered into the heart's atrial refractory period, at a time when such pulse is ineffective. This results in an effective prolongation of the P-to-V interval, which may either decrease hemodynamic performance and/or induce retrograde conduction. Even worse, the possibility exists that the atrial stimulus (delivered into the heart during the atrial refractory period) may induce atrial flutter or fibrillation.

Several approaches are known in the art to minimize the likelihood of a pacemaker-mediated tachycardia caused by the sensing of retrograde P-waves in patients having a dual-chamber pacing system. For example, a maximum tracking rate may be incorporated in modern DDD pacemakers. Another approach is Automatic Mode Switch that switches the pacing mode from any tracking mode (DDD or VDD) to a non-tracking mode. If the natural atrial rate exceeds this maximum tracking rate, the pacemaker converts to a non-tracking mode (known as a DDI mode). Sensing continues in both the atrium and the ventricle, but the ventricle is stimulated at a rate independent of the high atrial rate. If the atrial rate decreases again, the pacemaker may convert back to the ODD mode.

In order to detect pacemaker-mediated tachycardia, the time between the ventricular stimulation pulse and a sensed P-wave may be measured.

If a short, stable interval is measured, the sensed P-wave is suspected of being a retrograde P-wave. Corrective action may then be taken to terminate the pacemaker-mediated tachycardia, for example converting to an atrial non-tracking mode such as DDI.

Mounting clinical evidence supports the evolution of more complex cardiac stimulating devices capable of stimulating three or even all four heart chambers to stabilize arrhythmias or to re-synchronize heart chamber contractions (Ref: Cazeau S. et al., "Four chamber pacing in dilated cardiomyopathy, Pacing Clin. Electrophsyiol 1994 17(11 Pt 2):1974–9). Stimulation of multiple sites within a heart chamber has also been found effective in controlling arrhythmogenic depolarizations (Ref:

Ramdat-Misier A., et al., "Multisite or alternate site pacing for the prevention of atrial fibrillation," Am. J. Cardiol., 1999 11, 83(5b):237D–240D). In these multi-site or multi-chamber stimulation applications, correct synchronization of all heart chambers is vital to achieving a desired hemodynamic benefit. However, the occurrence of retrograde P-waves during biventricular or multi-site ventricular stimulation may lead to pacemaker-mediated tachycardia in the same way as described for dual chamber pacemakers. Retrograde P-waves may arise from more than one ventricular stimulation site. Therefore, in multi-site and multi-chamber stimulation devices, detection of retrograde P-waves and prevention of pacemaker-mediated tachycardia is just as important as in dual chamber devices.

The ability to detect the presence of retrograde P-waves during stimulation of more than one site within the ventricles, however, becomes more complex than in dual chamber stimulation because the retrograde P-waves may be arising from more than one retrograde pathway, each with a different conduction time. Sensed retrograde P-waves will increase the detected atrial rate indicating an atrial tachycardia when in fact there is none causing the stimulation device to deliver or withhold stimulation inappropriately. Sensed retrograde P-waves may also induce pacemaker-mediated tachycardia. Both of these situations are highly undesirable. What is needed, therefore, is a method for detecting retrograde P-waves during biventricular or multi-site ventricular stimulation and determining the site of ventricular stimulation associated with the retrograde conduction.

SUMMARY

The present invention addresses this need by providing an implantable cardiac stimulation device capable of stimulating at two or more ventricular sites and possessing a retrograde conduction detection algorithm. The retrograde conduction detection algorithm is executed whenever a pacemaker-mediated tachycardia is suspected.

The retrograde conduction detection algorithm (or routine) detects the presence of two or more retrograde conduction pathways arising from two or more ventricular stimulation sites. The retrograde conduction detection algorithm will effectively terminate a pacemaker-mediated tachycardia due to the presence of one retrograde conduction pathway. If two retrograde conduction pathways are identified, automatic adjustment of the stimulation device operating parameters is made to terminate the pacemaker-mediated tachycardia and prevent inappropriate arrhythmia detection.

The present invention provides an implantable cardiac stimulation device equipped with cardiac data acquisition capabilities. A preferred embodiment of the stimulation device includes a control system for controlling the operation of the device; a set of leads for receiving cardiac signals and for delivering atrial and ventricular stimulation pulses; a set of sensing circuits comprised of sense amplifiers for sensing and amplifying the cardiac signals; a sampler, such as an A/D converter for sampling cardiac signals; and pulse generators for generating atrial and ventricular stimulation pulses. In addition, the stimulation device includes a memory for storing operational parameters for the control system, such as cardiac signal sampling parameters and timing intervals such as AV and PV delays, and measured cardiac signal intervals. The device also includes a telemetry circuit for communicating with an external programmer.

When operating according to a preferred embodiment, the retrograde conduction detection algorithm sets the PV delays for each ventricular stimulation site to temporary test settings that are not equal to each other. Ventricular stimulation is delivered in an alternating fashion to the ventricular stimulation sites. If only one retrograde path exists, alternating the stimulation will effectively terminate a pacemaker-mediated tachycardia.

To detect if two retrograde conduction pathways exist, the mean interval from a ventricular stimulation pulse to the subsequent sensed P-wave (VP interval) is measured for each stimulation site. The standard deviations of the mean VP intervals for each ventricular stimulation site are then compared to a minimum acceptable value. If the standard deviation is small, retrograde conduction is detected for the corresponding ventricular stimulation site.

Retrograde conduction from two or more sites is further confirmed by a mathematical relationship examining the change in atrial rate relative to the change in VP intervals. If retrograde conduction is confirmed for two or more pathways, automatic adjustment of operating parameters, preferably an extension of the post-ventricular atrial blanking period, is made to terminate the pacemaker-mediated tachycardia. Adjustments are also made to prevent inappropriate arrhythmia detection due to the pacemaker-mediated tachycardia.

The stimulation device measures the time delay between the pacing of a ventricular site to the sensed P-wave in the corresponding atrium. The standard deviations of these retrograde conduction times for each ventricular sites are used to derive VP interval stability for different retrograde paths. The study of the relationship between average retrograde conduction stability and atrial heart rate within a few cardiac cycles confirms and identifies the source(s) of other retrograde conduction paths in existence. The identification of the retrograde paths enhances the response of the stimulation device to terminate a PMT, and helps qualify the atrial rate information used by the cardioverter to discriminate supraventricular tachyarrhythmia from ventricular tachyarrhythmia.

The system and method of the present invention thus provide a method for detecting retrograde conduction pathways arising from more than one ventricular stimulation site. The present invention further provides a safe, effective method of terminating pacemaker-mediated tachycardia due to retrograde conduction arising from one or more ventricular stimulation sites. By appropriately detecting a pacemaker-mediated tachycardia due to retrograde conduction, accurate arrhythmia detection for the purposes of cardioversion or shocking therapy is also improved.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout. The present invention is directed at detecting retrograde conduction in an implantable cardiac stimulating device possessing pacing, cardioversion and defibrillation capabilities. A general cardiac stimulation device will thus be described in conjunction with FIGS. 1 and 2, in which the retrograde conduction detection feature of the present invention could be implemented. It is recognized, however, that numerous variations of such a device exist in which the methods of the present invention could be implemented without deviating from the scope of the present invention.

Figure 1:
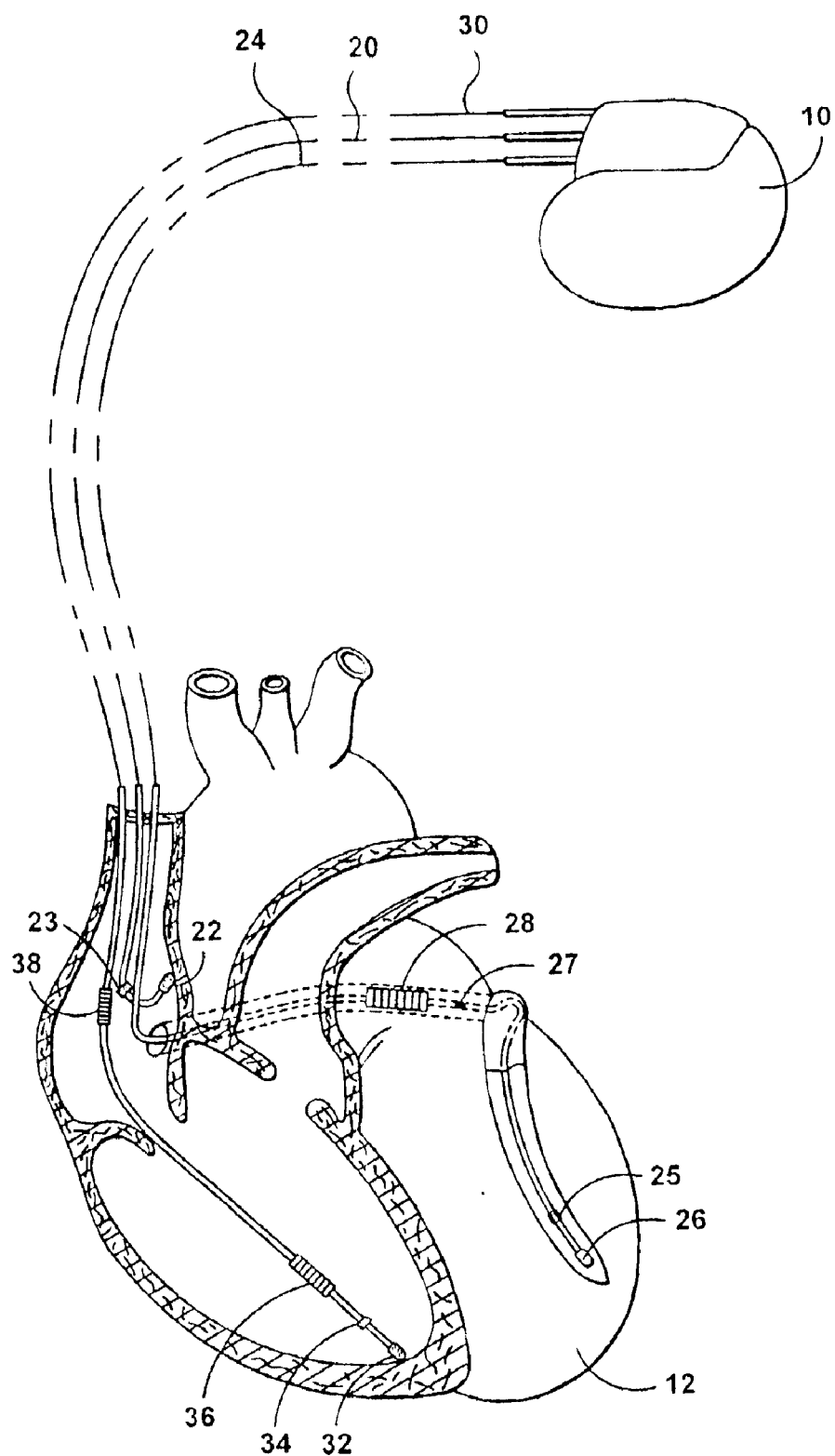
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. In an alternative embodiment, the coronary sinus lead 24 may also include a left ventricular ring electrode 25.

For a more detailed description of a coronary sinus lead, reference is made, for example, to U.S. patent application Ser. No. 09/457,277, titled "A Self-Anchoring, Steerable Coronary Sinus Lead" (Pianca et al.); and U.S. Pat. No. 5,466,254, titled "Coronary Sinus Lead with Atrial Sensing Capability" (Helland).

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
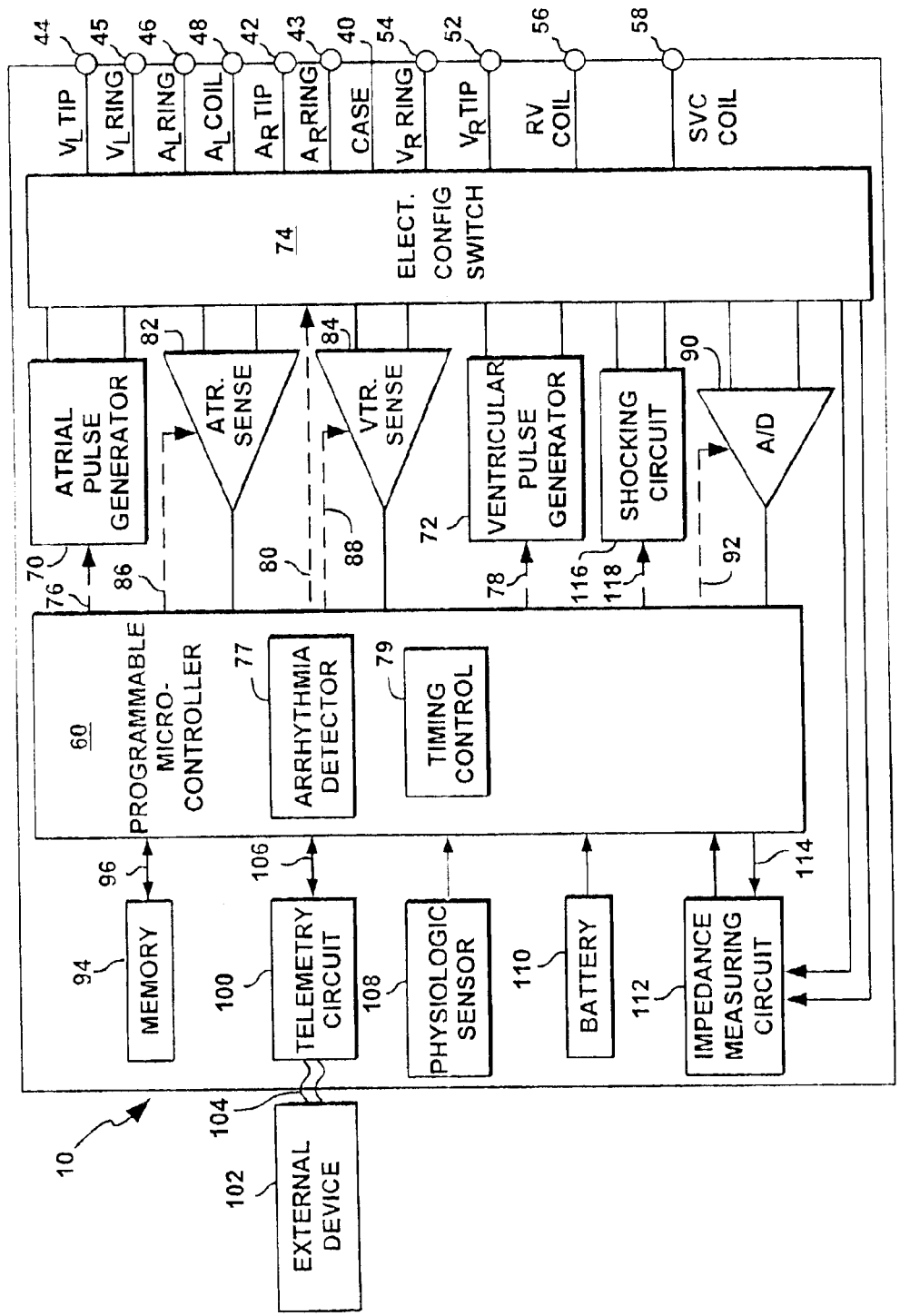
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector having a plurality of terminals 42, 43, 44, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal (AR TIP) 42 adapted for connection to the atrial tip electrode 22. The connector may also include a right atrial ring terminal (AR RING) 43 for connection to the atrial ring electrode 23.

To achieve left chamber sensing, pacing, and shocking, the connector includes at least a left ventricular tip terminal ($V_L$ TIP) 44, a left atrial ring terminal ($A_L$ RING) 46, and a left atrial shocking coil terminal ($A_L$ COIL) 48, which are adapted for connection to the left ventricular tip electrode 26, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the present invention include the microprocessor-based control system of U.S. Pat. No. 4,940,052 (Mann et. al). For a more detailed description of the various timing intervals used within the stimulation device and their interrelationship, reference is made to U.S. Pat. No. 4,788,980 (Mann et. al).

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches (not shown) as is known in the art.

Atrial sensing circuits (ATR. SENSE) 82 and ventricular sensing circuits (VTR. SENSE) 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Stimulation during pacing can be performed in a bipolar mode in devices combining pacing and cardioversion/defibrillation functions because unipolar stimulation may interfere with arrhythmia detection.

Hence, in one embodiment of the present invention, the switch bank 74 is configured such that: right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27. Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. The electrode combinations used for pacing and sensing are not critical to the present invention. Rather, any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation of the present invention. Each sensing circuit, 82 and 84, preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation. For a more detailed description of a sensing circuit, reference is made to U.S. Pat. No. 5,573,550, titled "Implantable Stimulation Device having a Low Noise, Low Power, Precision Amplifier for Amplifying Cardiac Signals" (Zadeh et. al.). For a more detailed description of an automatic sensitivity control system, reference is made to U.S. Pat. No. 5,685,315, titled "Cardiac Arrhythmia Detection System for an Implantable Stimulation Device" (McClure et. al).

The outputs of the atrial and ventricular sensing circuits, 82 and 84, are connected to the microcontroller 60 for triggering or inhibiting the atrial and ventricular pulse generators 70 and 72, respectively, in a demand fashion, in response to the absence or presence of cardiac activity in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy"). Discrimination algorithms may be employed in order to distinguish supraventricular tachycardia from ventricular tachycardia.

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) the energy level would be decreased until capture is lost. The lowest value at which capture still occurs is known as the capture threshold. Thereafter, a working margin is added to the capture threshold. The implementation of capture detection circuitry and algorithms are well known.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device. According to the methods included in the present invention, data will be collected and stored in memory to be analyzed for the detection of retrograde conduction. The results of this analysis are used for programming device 10 operating parameters for terminating a pacemaker-mediated tachycardia.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected. Accordingly, the stimulation device 10 can employ lithium/silver vanadium oxide batteries.

As further illustrated in FIG. 2, the stimulation device 10 is shown to include an impedance measuring circuit 112 that is enabled by the microcontroller 60 by means of a control signal 114.

It is a function of the stimulation device 10 to operate as an implantable cardioverter/defibrillator (ICD) device. That is, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV coil electrode 36, or as part of a split electrical vector using the SVC coil electrode 38 or the left atrial coil electrode 28 (i.e., using the RV coil electrode 36 as a common electrode).

Cardioversion shocks are generally considered to be of low to moderate energy level (so as to minimize pain felt by the patient), and/or synchronized with an R-wave and pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
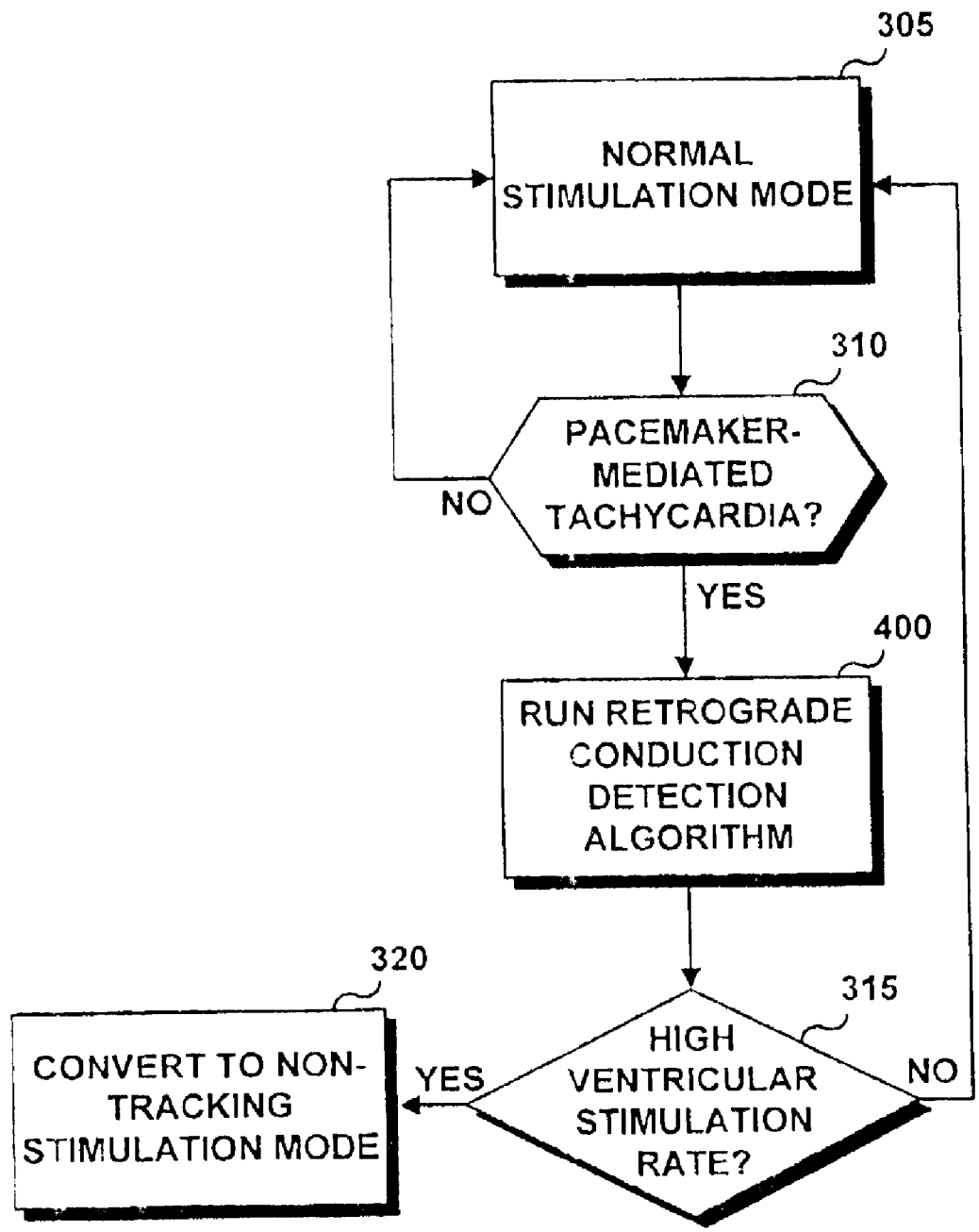
FIG. 3 is a flow chart providing an overview of the operations included in the present invention for responding to a high atrial rate in the device of FIG. 2.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

FIG. 3 shows that initially the device 10 is operating normally in the programmed mode for delivering stimulation therapy at step 305. If at any time during the normal stimulation mode, a pacemaker-mediated tachycardia is suspected, as determined at decision step 310, a retrograde conduction detection algorithm is executed at step 400. The retrograde conduction detection algorithm will be described in detail in conjunction with FIG. 4. The criteria used at decision step 310 for determining when a pacemaker-mediated tachycardia is suspected are predefined. For example, if the ventricular stimulation rate exceeds a defined rate limit during atrial sensing for a given number of consecutive cardiac cycles, pacemaker-mediated tachycardia is suspected. If the ventricular stimulation rate remains high after the retrograde conduction detection algorithm, the device 10 automatically switches to a non-tracking mode at step 320. In some cases, pacemaker-mediated tachycardia will be terminated during the execution of the retrograde conduction detection algorithm 400. In such cases the device 10 may immediately return to the normal stimulation mode 305.

Figure 4:
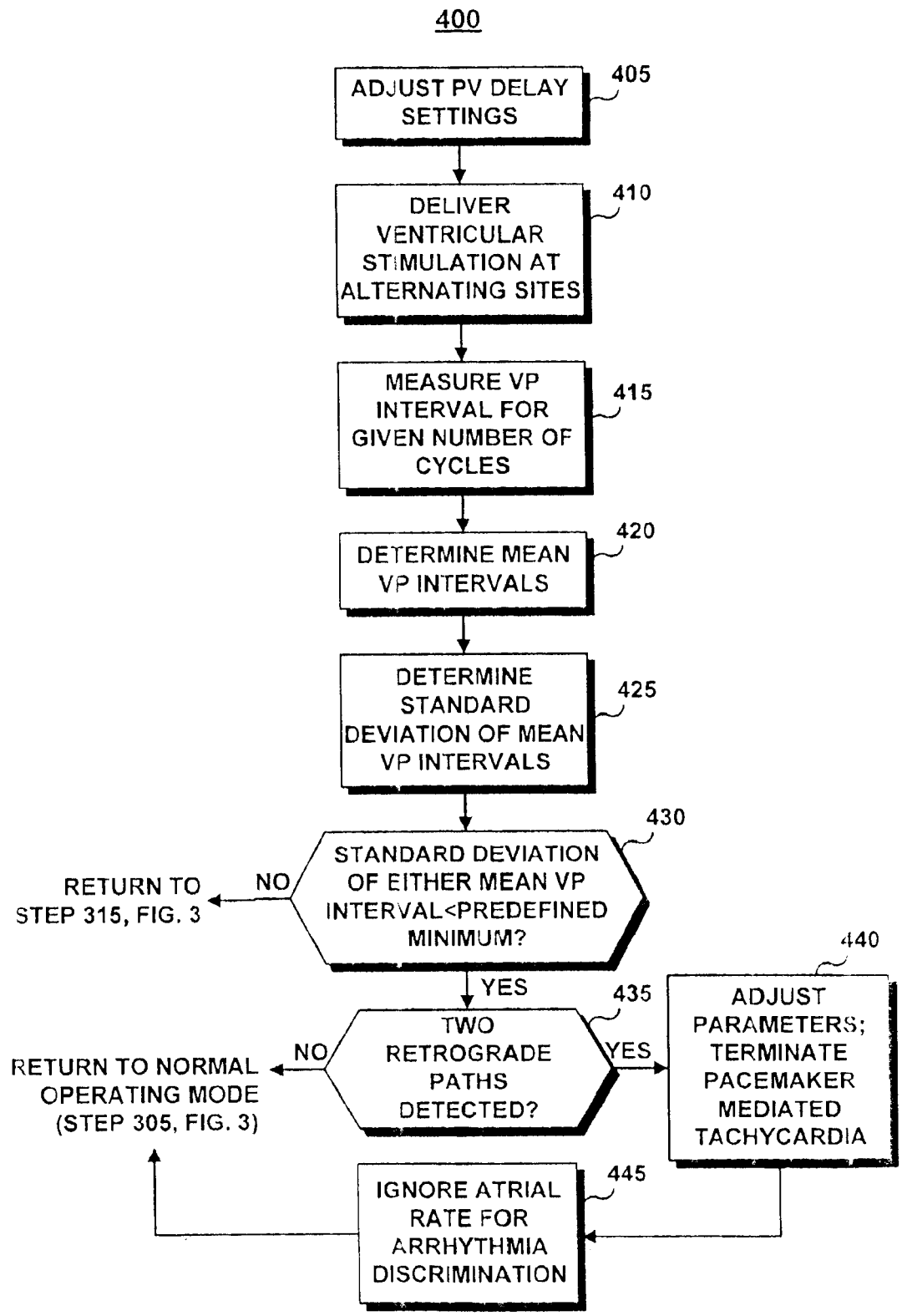
FIG. 4 is a flow chart depicting the method used in the operations of FIG. 3 for determining if a sensed high atrial rate is caused by retrograde conduction.

The retrograde conduction detection algorithm 400 is shown in FIG. 4. The algorithm begins at step 405 wherein the PV delays corresponding to each ventricular stimulation site are adjusted to predefined test PV delay settings. The PV delay for the first stimulation site, referred to as $PV_1$, is set to a different value than the PV delay for the second stimulation site, referred to as $PV_2$. For example, the $PV_1$ delay may be set to 150 msec, and the $PV_2$ delay may be set to 130 msec. Ventricular stimulation is then delivered to each stimulation site in an alternating fashion at step 410: on the first cycle stimulation is delivered to the first stimulation site after a $PV_1$ delay, and, on the subsequent cardiac cycle, stimulation is delivered to the second stimulation site after a $PV_2$ delay.

If only one retrograde pathway is present, alternating the delivery of stimulation between the two stimulation sites will terminate a pacemaker-mediated tachycardia. For example, if retrograde conduction is arising from the second ventricular stimulation site, stimulation at only the first ventricular stimulation site on one cardiac cycle will stop the retrograde conduction from arising from the second site for that cycle. This will allow the naturally occurring P-wave to be sensed during the subsequent cycle. If no intrinsic P-wave is detected, an atrial stimulation pulse will be delivered. Thus, the retrograde conduction detection algorithm 400 will effectively terminate a pacemaker-mediated tachycardia due to retrograde conduction arising from one ventricular stimulation site.

The ventricular stimulation pulses are delivered in an alternate fashion for a predefined number of cardiac cycles, e.g. eight cardiac cycles, at step 410. The intervals from each ventricular stimulation pulse to the subsequent P-wave, hereafter referred to as a "VP interval," are measured at step 415. At step 420 the mean VP intervals are determined. All VP intervals associated with the first ventricular stimulation site are averaged to determine a mean $V_1P$ interval. All VP intervals associated with the second ventricular stimulation site are averaged to determine a mean $V_2P$ interval.

The standard deviation of the mean $V_1P$ interval and the standard deviation of the mean $V_2P$ interval are then calculated at step 425. If retrograde conduction is present, the standard deviations of the mean VP intervals are expected to be small because retrograde conduction time is expected to be constant. The standard deviations are compared to a minimum value at step 430. If the standard deviations are less than the minimum value, two retrograde conduction paths are detected for the corresponding stimulation sites. If only one retrograde conduction pathway was present, a pacemaker-mediated tachycardia will have been terminated in the first two alternating stimulation cycles, therefore no retrograde conduction will be found.

If the standard deviations are not less than the predefined minimum, then no retrograde conduction is detected. The algorithm 400 returns to step 315 of FIG. 3. If high rate ventricular stimulation is still occurring, the operating mode is switched to a non-tracking mode. It is presumed that the high ventricular rate is associated with a high intrinsic atrial rate. If the high ventricular stimulation rate continues during atrial sensing (PV mode), the retrograde conduction detection algorithm will be repeated after a predefined number of PV cycles. If the intrinsic atrial rate remains persistently high, the programmed maximum tracking rate will limit the ventricular stimulation rate.

The standard deviation of the VP interval is one indication of the presence of retrograde conduction, however, the change in atrial rate with respect to a corresponding VP interval should also be examined to verify retrograde conduction. Changes in the ventricular rate due to an activity sensor-indicated rate or a maximum tracking rate can cause variations in the PV interval of one heart cycle that subsequently affects the following VP interval. Thus appropriate variations in the PV interval due to ventricular-based timing in a DDD stimulation mode could result in small variation of the VP interval without the presence of retrograde conduction. Thus, if retrograde conduction was identified at step 430 of FIG. 4 according to the minimum standard deviation criteria, the existence of two retrograde conduction paths is further confirmed at decision step 435 by calculating the following relation between the atrial intervals and the VP intervals:

If $|P_2P_3-P_1P_2|-2\times|\text{mean}V_1P-\text{mean}V_2P|<X$, then two retrograde paths, (1)

where $P_2P_3$ represents the time interval from the second atrial sensed P-wave to the third atrial sensed P-wave;

$P_1P_2$ represents the time interval from the first atrial sensed P-wave to the second atrial sensed P-wave;

MeanV$_1$P represents the mean of the V$_1$P interval;

MeanV$_2$P represents the mean of the V$_2$P interval; and

X represents a predefined programmable tolerance in milliseconds, preferably on the order of 20 msec.

If the difference between the two atrial sensed cycle intervals is less than a predefined amount greater than twice the difference between the two mean VP intervals, two retrograde conduction paths exist. Equation (1) is the difference between the following two equations:

$$(2)\ P_1P_2 = \text{Ventricular Rate} - V_1P + V_2P$$

$$(3)\ P_2P_3 = \text{Ventricular Rate} - V_2P + V_1P$$

Thus the change in the atrial rate from the first PV cycle to the second PV cycle ($P_2P_3 - P_1P_2$) is compare to the change in the VP intervals. If the change in the atrial rate less the change in the VP intervals is less than a predefined tolerance, then two retrograde conduction paths are confirmed at step 435.

If the relation of Equation (1) is not true, then one or no retrograde conduction exists. If only one retrograde conduction path was present, the retrograde conduction detection algorithm will have successfully terminated the pacemaker-mediated tachycardia by alternating ventricular stimulation sites. If the atrial rate changes account for the small variation in VP intervals, then no retrograde conduction can be confirmed. Therefore device 10 may return to its normal operating mode, step 305 (FIG. 3).

Figure 5:
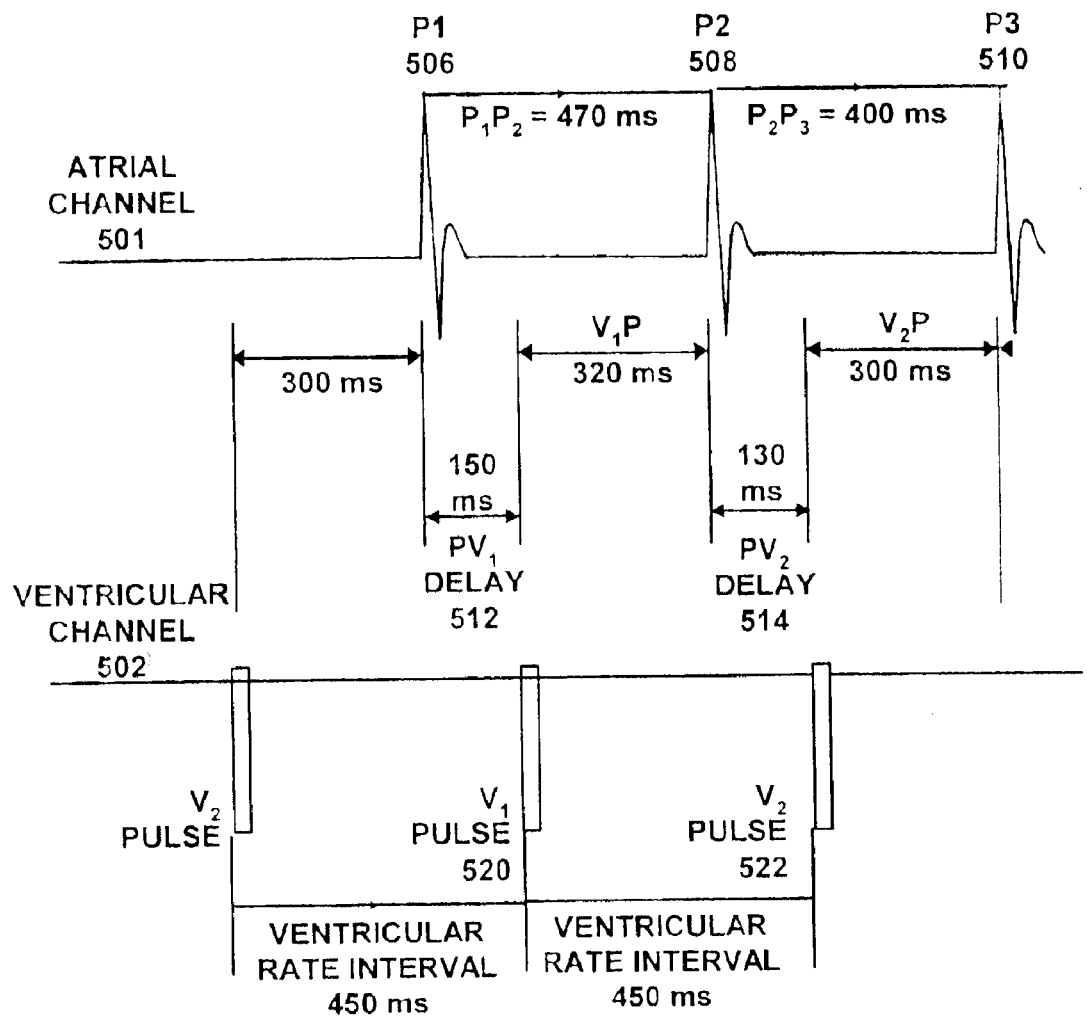
FIG. 5 is a timing diagram illustrating a sequence of atrial and ventricular events occurring during the retrograde conduction detection algorithm of FIG. 4.

The timing diagram shown in FIG. 5 illustrates the relationship of the timing intervals used in the calculation of Equation (1). On the atrial channel 501, three consecutive P-waves are shown, P$_1$, P$_2$, and P$_3$, 506, 508, 510, respectively. The first atrial P-wave, P$_1$ 506, is followed by the PV$_1$ delay 512 and a ventricular stimulation pulse, V$_1$ 520 (shown on the ventricular channel 502), which is delivered to a first ventricular stimulation site. The second atrial P-wave, P$_2$ 508, is followed by a PV$_2$ delay 514 and a ventricular stimulation pulse V$_2$ 522, which is delivered to a second ventricular stimulation site. In this example, the PV$_1$ delay 512 is set to 150 msec, and the PV$_2$ delay 514 is set to 130 msec. The calculation according to equation 1 for the example intervals shown in FIG. 5 is:

$$|430-470|-2\times|320-300|=40-40=0$$

Therefore, in this example, retrograde conduction is occurring from both ventricular stimulation sites since the relationship between the change in the atrial rate and the change in the VP intervals does not exceed the minimum allowed tolerance.

As shown in FIG. 4, if two retrograde conduction paths are confirmed at step 435, then automatic adjustment of device 10 operating parameters is made to terminate the pacemaker-mediated tachycardia at step 440. In a preferred embodiment, if device 10 is a multi-chamber pacemaker, the post-ventricular atrial refractory period (referred to as PVARP) is extended. Preferably, PVARP is adjusted to be greater than the longer of the two retrograde conduction times, i.e. longer than the greatest mean VP interval. In this way, a retrograde conducted P-wave will occur during the PVARP and not be tracked for ventricular stimulation purposes. Instead, the next intrinsic atrial P-wave occurring after the extended PVARP will be sensed or an atrial stimulation pulse will be delivered thus terminating the pacemaker-mediated tachycardia.

If device 10 is also a cardioverter defibrillator and retrograde conduction is detected, the detected atrial rate interval is ignored at step 445 if the algorithm for discriminating between supraventricular tachycardia and ventricular tachycardia is enabled. In this way, the retrograde conduction is not inappropriately detected as a supraventricular tachycardia potentially triggering inappropriate therapy delivery. Having detected both retrograde conduction pathways and taken appropriate action for terminating a pacemaker-mediated tachycardia, device 10 may now return to the normal operating mode 305 (FIG. 3)

Thus, a system and method for detecting retrograde conduction from one or more ventricular stimulation sites during biventricular or multi-site ventricular stimulation. By identifying which ventricular stimulation sites are associated with a retrograde conduction pathway, appropriate action can be taken to terminate a pacemaker-mediated tachycardia. Furthermore, confirmation and termination of a pacemaker-mediated tachycardia will prevent an inappropriate arrhythmia detection and inappropriate cardioversion or shock therapy from being delivered. While the present invention has been described according to specific embodiments, this description is intended for illustration and not limitation. Those skilled in the art may modify features or methods described herein without departing from the scope of the present invention.

What is claimed is:

1. In an implantable cardiac stimulation device, a method comprising:

delivering stimulation energy to at least two ventricular sites during at least some cardiac cycles;

detecting that a potential pacemaker-mediated tachycardia condition exists; and alternating the delivery of stimulation energy to the at least two ventricular sites during subsequent cardiac cycles to terminate a retrograde conduction arising from one of the at least two ventricular sites.

2. The method of claim 1, further comprising determining average V-P intervals for the at least two ventricular sites, determining respective measures of variability for the respective V-P intervals, comparing the measures of variability with a threshold value, and determining that retrograde conduction exists for each ventricular site if the measures of variability fall below the threshold.

3. The method of claim 2, further comprising determining that no retrograde conduction exists if the measures of variability exceed the threshold.

4. The method of claim 2, wherein determining a measure of variability comprises determining a standard deviation for the V-P intervals corresponding to each ventricular site.

5. The method of claim 1, wherein alternating the delivery of stimulation energy comprises delivering stimulation energy to only one ventricular site per cardiac cycle.

6. The method of claim 2, wherein upon confirming retrograde conduction for the at least two ventricular sites, automatically adjusting an operating parameter.

7. The method of claim 6, wherein automatically adjusting an operating parameter comprises extending a post-ventricular atrial blanking period.

8. An implantable cardiac stimulation device comprising:

a sensor that is operative to detect cardiac activity;

a pulse generator that is operative to generate stimulation pulses to be delivered to at least two ventricular sites during normal cardiac cycles; and a control circuit that is coupled to the sensor and that is operative to detect a potential pacemaker-mediated tachycardia condition based on the cardiac activity sensed by the sensor, wherein the control circuit is operative to control the pulse generator to alternate the stimulation of the at least two ventricular sites during subsequent cycles to terminate a retrograde conduction arising from one of the at least two ventricular sites.

9. The device of claim 8, wherein the control circuit is operative to determine average V-P intervals for the at least two ventricular sites, determine respective measures of variability for the respective V-P intervals, compare the measures of variability with a threshold value, and determine that retrograde conduction exists for each ventricular site if the measures of variability fall below the threshold.

10. The device of claim 9, wherein the control circuit is operative to determine that no retrograde conduction exists if the measures of variability exceed the threshold.

11. The device of claim 9, wherein the control circuit is operative to determine a standard deviation for the V-P intervals corresponding to each ventricular site.

12. The device of claim 8, wherein the control circuit is responsive to the potential pacemaker-mediated tachycardia condition to deliver stimulation energy to one ventricular site per cardiac cycle.

13. The device of claim 9, wherein the control circuit is responsive to detecting retrograde conduction for the at least two ventricular sites to automatically adjust an operating parameter.

14. The device of claim 13, wherein the operating parameter comprises a post-ventricular atrial blanking period.

15. An implantable cardiac stimulation device comprising:

means for delivering substantially concurrent ventricular stimulation pulses to at least two ventricular sites during at least some cardiac cycles;

means for detecting a potential retrograde conduction condition; and means for alternating the stimulation of the two or more ventricular stimulation sites to terminate a retrograde conduction arising from one of the at least two ventricular sites.

16. The device of claim 15, further comprising means for determining average V-P intervals for the at least two ventricular sites, means for determining respective measures of variability for the respective V-P intervals, means for comparing the measures of variability with a threshold value, and means for detecting that retrograde conduction exists for each ventricular site if the measures of variability fall below the threshold.

17. The device of claim 16, further comprising means for determining that no retrograde conduction exists if the measures of variability exceed the threshold.

18. The device of claim 15, wherein the means for alternating comprises means for delivering stimulation energy to one ventricular site per cardiac cycle.

19. The device of claim 16, further comprising means for adjusting an operating parameter in response to the means for detecting retrograde conduction.

20. The device of claim 19, wherein the means for adjusting an operating parameter comprises means for adjusting a post-ventricular atrial blanking period.

* * * * *